United States Patent [19]
Evans et al.

[11] Patent Number: 4,737,578
[45] Date of Patent: Apr. 12, 1988

[54] HUMAN INHIBIN

[75] Inventors: Ronald M. Evans; Michael G. Rosenfeld, both of San Diego; Gail Cerelli, Cardiff, all of Calif.; Kelly E. Mayo, Wilmette, Ill.; Joachim Spiess, Encinitas, Calif.; Jean E. F. Rivier, La Jolla, Calif.; Wylie W. Vale, Jr., La Jolla, Calif.

[73] Assignee: The Salk Institute for Biological Studies, San Diego, Calif.

[21] Appl. No.: 848,924

[22] Filed: Apr. 7, 1986

Related U.S. Application Data

[63] Continuation-in-part of Ser. No. 828,435, Feb. 10, 1986, abandoned.

[51] Int. Cl.$^4$ .......................... C07K 7/10; C07K 13/00
[52] U.S. Cl. ...................................... 530/350; 530/324
[58] Field of Search ................................ 530/350, 324

[56] References Cited

PUBLICATIONS

Chem. Abstr., vol. 94 (1981), 187299.
Chem. Abstr., vol. 92 (1980), 2711.
Chem. Abstr., vol. 92 (1980), 106678.
Chem. Abstr., vol. 90 (1979), 99634.
Chem. Abstr., vol. 105 (1986), 127623.
Chem. Abstr., vol. 103 (1985), 65677.
Chem. Abstr., vol. 103 (1985), 98880.
Chem. Abstr., vol. 103 (1985), 172217.
Chem. Abstr., vol. 98 (1983), 28231.
A. J. Mason et al., "Complementary DNA Sequences of Ovarian Follicular Fluid Inhibin Show Precursor Structure and Homology with Transforming Growth Factor-B", *Biochem. Biophys. Res. Commun.*, 135, 957–964 (1986).
A. J. Mason et al., "Structure of Two Human Ovarian Inhibins", *Nature*, 318, 659–663 (1985).

*Primary Examiner*—Delbert R. Phillips
*Attorney, Agent, or Firm*—Fitch, Even, Tabin & Flannery

[57] ABSTRACT

Proteins with inhibin activity having a weight of about 32,000 daltons. The molecule is composed of two chains having molecular weights of about 18,000 and about 14,000 daltons, respectively, which are bound together by disulfide bonding. The 18K chain is obtained from the human inhibin gene and has the formula: H-Ser-Thr-Pro-Leu-Met-Ser-Trp-Pro-Trp-Ser-Pro-Ser-Ala-Leu-Arg-Leu-Leu-Gln-Arg-Pro-Pro-Glu-Glu-Pro-Ala-Ala-His-Ala-Asn-Cys-His-Arg-Val-Ala-Leu-Asn-Ile-Ser-Phe-Gln-Glu-Leu-Gly-Trp-Glu-Arg-Trp-Ile-Val-Tyr-Pro-Pro-Ser-Phe-$R_{65}$-Phe-His-Tyr-Cys-His-Gly-Gly-Cys-Gly-Leu-His-Ile-Pro-Pro-Asn-Leu-Ser-Leu-Pro-Val-Pro-Gly-Ala-Pro-Pro-Thr-Pro-Ala-Gln-Pro-Tyr-Ser-Leu-Leu-Pro-Gly-Ala-Gln-Pro-Cys-Cys-Ala-Ala-Leu-Pro-Gly-Thr-Met-Arg-Pro-Leu-His-Val-Arg-Thr-Thr-Ser-Asp-Gly-Gly-Tyr-Ser-P e-Lys-Tyr-Glu-Thr-Val-Pro-Asn-Leu-Leu-Thr-Gln-His-Cys-Ala-Cys-Ile-OH, wherein $R_{65}$ is Ile or Arg. The 18K chain is connected by disulfide bonding to the 14K chain.

7 Claims, No Drawings

HUMAN INHIBIN

This invention was made with Government support under Grants Nos. HD-13527 and AM-26741 and under Contract No. NO1-HD-3-2826 awarded by the National Institutes of Health. The Government has certain rights in this invention.

This application is a continuation-in-part of our earlier application Ser. No. 828,435, filed Feb. 10, 1986, now abandoned.

The present invention relates to a protein having inhibin activity

BACKGROUND OF THE INVENTION

The existence of inhibin as a water-soluble substance of gonadal origin which acts specifically at the pituitary level to suppress the secretion of follicle-stimulating hormone (FSH) was postulated by McCullagh more than 50 years ago, *Science*, 76, 19–20 (1932). There has been great interest in it, and many laboratories have attempted to isolate and characterize this substance. Many reports have appeared in the literature claiming the purification of inhibin-like material; however subsequent studies have shown that these substances were either not homogenous or did not have the high specific activity of true inhibin. Inhibin may be used to regulate fertility, gonadotropin secretion or sex hormone production in mammalians, both females and particularly males.

SUMMARY OF THE INVENTION

In accordance with the present invention, two proteins are provided, both having a molecular weight of about 32,000 daltons and exhibiting inhibin activity. Such a protein can be isolated from ovarian follicular fluid, from seminal plasma and/or from placental fluid. Such a protein can also be synthesized and can be produced using recombinant DNA technology The proteins are hereinafter referred to as Protein A and Protein B. Each has a molecular weight of about 32,000 daltons (32K) and is composed of two polypeptide chains having molecular weights of 18,000 and 14,000 daltons, respectively; the chains being linked together in the biologically active protein by disulfide bonding. Each 32K protein exhibits inhibin activity in basal secretion of FSH but not inhibiting basal secretion of luteinizing hormone (LH).

DETAILED DESCRIPTION OF THE PREFERRED EMBODIMENTS

Each 32,000 dalton protein (Protein A and Protein B) is composed of two chains of 18K and 14K, respectively, and the chains of the intact molecule are held together by disulfide bonding, the linkage between the chains may be necessary for biological activity. The 18K chain of each protein has exactly the same sequence of 134 amino acid residues and has a free acid C-terminus.

Protein A includes a 134-residue chain (the 18K chain) that is linked by one or more disulfide bridges to a 116-residue chain (the 14K chain) which may include an internal disulfide bridge. Protein B has the same 18K chain linked to a homologous 14K chain.

The 32K protein is acidic and exhibits inhibin activity in that it specifically inhibits basal secretion of FSH in a rat anterior pituitary monolayer culture system. Each 32K protein is useful for regulating fertility of mammalian animals.

Human inhibin is isolated from crude extract material obtained from human follicular fluid. Other appropriate bodily extracts, such as seminal plasma and placenta or ovarian fluids, may also be used. Successive purification procedures are used that include immunoaffinity chromatography followed by gel filtration or permeation Fast Protein Liquid Chromatography (FPLC) and Reverse Phase-High Performance Liquid Chromatography (? ? -HPLC) using a suitable stationary phase and mobile phase. The immunoaffinity chromatography purification process employs antibodies raised against a peptide based either upon porcine inhibin or human inhibin. The same procedure can be used to obtain inhibin protein from a crude extract product of a recombinant DNA process. The extraction and purification procedure set forth in *B.B.R.C.* 133, 1, Nov. 27, 1985, which is incorporated herein by reference, can also be used.

Porcine inhibin was earlier isolated to substantial purity from porcine follicular fluid using heparin-Sepharose affinity chromatography, followed by gel filtration on Sephacryl S-200 gel and then successive RP-HPLCs and FPLCs, as set forth in detail in pending U.S. patent application Ser. No. 796,300, filed Nov. 8, 1985, the disclosure of which is incorporated by reference. The formulae for porcine inhibin A and B are set forth in Mason et al., *Nature*, 318, December 19/26, 1985, pp 659–663.

By using a portion of the sequence of any chain of inhibin protein, the mRNA encoding that chain can be isolated, and the cDNA can be synthesized by recombinant DNA techniques. Messenger RNA (mRNA) is obtained from ovarian follicules or from placental tissues which produce inhibin, and then cDNA is synthesized from the mRNA by reverse transcription. The cDNA is inserted into a cloning vector which is used to transform a suitable host to create a cDNA library.

Based upon the known partial amino acid residue sequence of the inhibin chain, labelled oligonucleotides are synthesized for detecting cDNA corresponding to chain. Because of the degeneracy of the genetic code, mixed hybridization probes can be prepared and used as probes. These probes are then used to select, from the library, cDNA clones that contain the gene sequences encoding the chain. cDNA libraries may also be screened by immunological expression assay with antibody raised against inhibin or one of the inhibin chains. Immunological expression assays may also be used to confirm screening with hybridization probes.

From selected clones, cDNA is excised and inserted into appropriate vectors under the control of appropriate promoter sequences, and the vectors are transformed into cell lines for expression of the recombinant inhibin chains. Vectors containing the genes for an appropriate pair of chains may conceivably be transformed into the same cell line; however it may be preferable to transform vectors for expression of each chain into separate cell lines. The individual inhibin chains can then be isolated from the cellular material and/or the cell culture medium to serve as intermediates for the preparation of bioactive inhibin. Appropriate quantities of the 18K and the 14K chains are then subjected to oxidizing conditions which promote disulfide bonding between the chains to produce inhibin.

To obtain a probe by which to screen for human inhibin-encoding cDNA's, an oligonucleotide is first synthesized based upon the N-terminal sequence of porcine inhibin. The N-terminal sequence of porcine inhibin was determined by extraction of porcine inhibin, purification and then sequence analysis. The entire sequence of an α-chain of porcine inhibin and two β-chains of porcine inhibin are set forth in Mason et al., *Nature*, Volume 318, pages 659–663 (Dec. 19/26, 1985), the disclosure of which is incorporated herein by reference. Using a procedure similar to that set forth in this article, clones are obtained which, by DNA sequence analysis, code for the entire α-chain of porcine inhibin. As disclosed in this article, the precursor protein consists of 364 amino acids, of which the C-terminal 134 amino acids constitute the α-chain of inhibin.

The DNA which codes for the porcine precursor is then separated to form single-stranded segments, which are in turn used as probes to screen a cDNA library constructed using mRNA obtained from human placenta using techniques such as those described in U.S. Pat. No. 4,549,986, issued October 29, 1985 to R. M. Evans and M. G. Rosenfeld, the disclosure of which is incorporated herein by reference.

Hybridizing cloned cDNA's are obtained, and sequence analysis confirms the existence of cDNA over 1.3 kilobases in length coding for a precursor containing 366 amino acids, of which the C-terminal 134 residues are considered to represent the α-chain of human inhibin, as set forth in Table I hereinafter. The 134-residue α-chain may exert inhibin activity independent of the β-chain; however, together the α and β-chains constitute a biologically active dimeric structure which can be isolated from body fluids. Moreover, the 366 residue precursor, which is useful as a source of the 134 residue α-chain, as well as N-terminally shortened versions thereof, may also exhibit inhibin activity.

Using the foregoing molecular biology technique to read the gene sequence encoding the inhibin α-chain, the α-chain of human inhibin has been characterized and been found to constitute a 134 residue chain having the following formula: H-Ser-Thr-Pro-Leu-Met-Ser-Trp-Pro-Trp-Ser-Pro-Ser-Ala-Leu-Arg-Leu-Leu-Gln-Arg-Pro-Pro-Glu-Glu-Pro-Ala-Ala-His-Ala-Asn-Cys-His-Arg-Val-Ala-Leu-Asn-Ile-Ser-Phe-Gln-Glu-Leu-Gly-Trp-Glu-Arg-Trp-Ile-Val-Tyr-Pro-Pro-Ser-Phe-R$_{65}$-Phe-His-Tyr-Cys-His-Gly-Gly-Cys-Gly-Leu-His-Ile-Pro-Pro-Asn-Leu-Ser-Leu-Pro-Val-Pro-Gly-Ala-Pro-Pro-Thr-Pro-Ala-Gln-Pro-Tyr-Ser-Leu-Leu-Pro-Gly-Ala-Gln-Pro-Cys-Cys-Ala-Ala-Leu-Pro-Gly-Thr-Met-Arg-Pro-Leu-His-Val-Arg-Thr-Thr-Ser-Asp-Gly-Gly-Tyr-Ser-Phe-Ly -Tyr-Glu-Thr-Val-Pro-Asn-Leu-Leu-Thr-Gln-His-Cys-Ala-Cys-Ile-OH, wherein R$_{65}$ is Ile or Arg. Table I illustrates the preferred embodiment wherein R$_{65}$ is Ile; when R$_{65}$ is Arg, it is preferably coded for by CGT.

The α-chain is linked by at least one disulfide bridge to a β-chain having either 116 residues or 115 residues. The β-chain may have the following 116-residue formula: H-Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro-Ser-Gly-Tyr-His-Ala-Asn-Tyr-Cys-Glu-Gly-Glu-Cys-Pro-Ser-His-Ile-Ala-Gly-Thr-Ser-Gly-Ser-Ser-Leu-Ser-Phe-His-Ser-Thr-Val-Ile-A n-His-Tyr-Arg-Met-Arg-Gly-His-Ser-Pro-Phe-Ala-Asn-Leu-Lys-Ser-Cys-Cys-Val-Pro-Thr-Lys-Leu-Arg-Pro-Met-Ser-Met-Leu-Tyr-Tyr-Asp-Asp-Gly-Gln-Asn-Ile-Ile-Lys-Lys-Asp-Ile-Gln-Asn-Met-Ile-Val-Glu-Glu-Cys-Gly-Cys-Ser-OH. Alternatively, the β-chain may have the following 115-residue formula: H-Gly-Leu-Glu-Cys-Asp-Gly-Arg-Thr-Asn-Leu-Cys-Cys-Arg-Gln-Gln-Phe-Phe-Ile-Asp-Phe-Arg-Leu-Ile-Gly-Trp-Ser-Asp-Trp-Ile-Ile-Ala-Pro-Thr-Gly-Tyr-Tyr-Gly-Asn-Tyr-Cys-Glu-Gly-Ser-Cys-Pro-Ala-Tyr-Leu-Ala-Gly-Val-Pro-Gly-Ser-Ala-Ser-Ser-Phe-His-Thr-Ala-Val-Val-A n-Gln-Tyr-Arg-Met-Arg-Gly-Leu-Asn-Pro-Gly-Thr-Val-Asn-Ser-Cys-Cys-Ile-Pro-Thr-Lys-Leu-Ser-Thr-Met-Ser-Met-Leu-Tyr-Phe-Asp-Asp-Glu-Tyr-Asn-Ile-Val-Lys-Arg-Asp-Val-Pro-Asn-Met-Ile-Val-Glu-Glu-Cys-Gly-Cys-Ala-OH.

Substantially pure 32K inhibin, which should have a purity of at least about 80 weight percent, and preferably at least about 90 weight percent, based upon total protein content, combined with a pharmaceutically acceptable carrier to form a pharmaceutical composition, may be administered to mammals, including humans, either intravenously, subcutaneously, percutaneously, intramuscularly or orally for control of fertility, gonadotropin secretion or sex hormone production.

Furthermore antibodies raised against synthetic fragments of inhibin, specifically the 6 N-terminal residues and the 25 N-terminal residues, have been shown to neutralize the activity of purified inhibin and raise plasma FSH levels in rats. Thus passive (administration of antibodies) or active (administration of immunogenic inhibin as antigen) immunoneutralization methods could be employed to block endogenous inhibin and thereby elevate endogenous gonadotropin secretion and evert a profertility effect in human beings and other vertebrate animal species having inhibin of a similar polypeptide structure. Administration of inhibin induces decreased fertility in female mammals and decreases spermatogenesis in male mammals. Administration of a sufficient amount of inhibin induces infertility in mammals. Inhibin is also useful for tests to diagnose infertility or other disorders of the reproductive system; for example polyclonal antibodies raised against the inhibin α-chain or against an N-terminal segment thereof can be used in a diagnostic assay to detect an unusually high or low level of human inhibin.

Antibodies to human inhibin (h Inhib) are made using synthetic fragments or analogs thereof coupled to carrier proteins by bis-diazotized benzidine or glutaraldehyde, as described in Vale et al. *Methods in Enzymology: Neuroendocrine Peptides*, pp. 565–577, Academic Press, New York, 1983; and Vale et al. *Methods in Enzymology: Neuroendocrine Peptides II*, Academic Press, in press, 1986. Specifically, to raise antibodies in rabbits against human inhibin [Gly$^{26}$, Tyr$^{27}$]-hInhib-(1-27) is conjugated to human α-globulins by bis-diazotized benzidine, and an emulsion with Freunds adjuvant is administered intradermally every two weeks. One week following the third injection, blood is removed and serum saved. [Gly$^{26}$, Tyr$^{27}$]-hInhib-(1–27) is iodinated by the chloramine T method; it is purified by cartridge extraction and HPLC for use as a tracer in human inhibin radioimmunoassays, as described in the two Vale et al. articles (the disclosure of which is incorporated herein by reference) for other neuroendocrine hormones.

As previously mentioned, such antibodies can be used to isolate native human inhibin from a suitable bodily extract, such as ovarian follicular fluid obtained from in vitro fertilization, using antibody affinity chromatography—as for example in accordance with the principles set forth in U.S. Pat. No. 4,341,761, issued July 27, 1982 or in U.S. Pat. No. 4,361,509, issued November 30, 1982, the disclosures of which are incorporated herein by reference.

TABLE I

```
GAAGGACTGGGGAAGACTGGATGAGAAGGGTAGAAGAGGGTGGGTGTGGGATGGGGAGGG

GAGAGTGGAAAGGCCCTGGGCAGACCCTGGCAGAAGGGGCACGGGGCAGGGTGTGAGTTC
                                                                     10
CCCACTAGCAGGGCCAGGTGAGCTATGGTGCTGCACCTACTGCTCTTCTTGCTGCTGACC
                                Met Val Leu His Leu Leu Leu Phe Leu Leu Leu Thr 20                                       30
CCACAGGGTGGGCACAGCTGCCAGGGGCTGGAGCTGGCCCGGGAACTTGTTCTGGCCAAG
Pro Gln Gly Gly His Ser Cys Gln Gly Leu Glu Leu Ala Arg Glu Leu Val Leu Ala Lys 40                                       50
GTGAGGGCCCTGTTCTTGGATGCCTTGGGGCCCCCCGCGGTGACCAGGGAAGGTGGGGAC
Val Arg Ala Leu Phe Leu Asp Ala Leu Gly Pro Pro Ala Val Thr Arg Glu Gly Gly Asp 60                                       70
CCTGGAGTCAGGCGGCTGCCCCGAAGACATGCCCTGGGGGGCTTCACACACAGGGGCTCT
Pro Gly Val Arg Arg Leu Pro Arg Arg His Ala Leu Gly Gly Phe Thr His Arg Gly Ser 80                                       90
GAGCCCGAGGAAGAGGAGGATGTCTCCCAAGCCATCCTTTTCCCAGCCACAGATGCCAGC
Glu Pro Glu Glu Glu Glu Asp Val Ser Gln Ala Ile Leu Phe Pro Ala Thr Asp Ala Ser 100                                      110
TGTGAGGACAAGTCAGCTGCCAGAGGGCTGGCCCAGGAGGCTGAGGAGGGCCTCTTCAGA
Cys Glu Asp Lys Ser Ala Ala Arg Gly Leu Ala Gln Glu Ala Glu Glu Gly Leu Phe Arg 120                                      130
TACATGTTCCGGCCATCCCAGCATACACGCAGCCGCCAGGTGACTTCAGCCCAGCTGTGG
Tyr Met Phe Arg Pro Ser Gln His Thr Arg Ser Arg Gln Val Thr Ser Ala Gln Leu Trp 140                                      150
TTCCACACCGGGCTGGACAGGCAGGGCACAGCAGCCTCCAATAGCTCTGAGCCCCTGCTA
Phe His Thr Gly Leu Asp Arg Gln Gly Thr Ala Ala Ser Asn Ser Ser Glu Pro Leu Leu 160                                      170
GGCCTGCTGGCACTGTCACCGGGAGGACCCGTGGCTGTGCCCATGTCTTTGGGCCATGCT
Gly Leu Leu Ala Leu Ser Pro Gly Gly Pro Val Ala Val Pro Met Ser Leu Gly His Ala 180                                      190
CCCCCTCACTGGGCCGTGCTGCACCTGGCCACCTCTGCTCTCTCTCTGCTGACCCACCCC
Pro Pro His Trp Ala Val Leu His Leu Ala Thr Ser Ala Leu Ser Leu Leu Thr His Pro 200                                      210
GTCCTGGTGCTGCTGCTGCGCTGTCCCCTCTGTACCTGCTCAGCCCGGCCTGAGGCCACG
Val Leu Val Leu Leu Leu Arg Cys Pro Leu Cys Thr Cys Ser Ala Arg Pro Glu Ala Thr 220                                      230
CCCTTCCTGGTGGCCCACACTCGGACCAGACCACCCAGTGGAGGGGAGAGAGCCCGACGC
Pro Phe Leu Val Ala His Thr Arg Thr Arg Pro Pro Ser Gly Gly Glu Arg Ala Arg Arg 240                                      250
TCAACTCCCCTGATGTCCTGGCCTTGGTCTCCCTCTGCTCTGCGCCTGCTGCAGAGGCCT
Ser Thr Pro Leu Met Ser Trp Pro Trp Ser Pro Ser Ala Leu Arg Leu Leu Gln Arg Pro 260                                      270
CCGGAGGAACCGGCTGCCCATGCCAACTGCCACAGAGTAGCACTGAACATCTCCTTCCAG
Pro Glu Glu Pro Ala Ala His Ala Asn Cys His Arg Val Ala Leu Asn Ile Ser Phe Gln 280                                      290
GAGCTGGGCTGGGAACGGTGGATCGTGTACCCTCCCAGTTTCATCTTCCACTACTGTCAT
Glu Leu Gly Trp Glu Arg Trp Ile Val Tyr Pro Pro Ser Phe Ile Phe His Tyr Cys His 300                                      310
GGTGGTTGTGGGCTGCACATCCCACCAAACCTGTCCCTTCCAGTCCCTGGGGCTCCCCCT
Gly Gly Cys Gly Leu His Ile Pro Pro Asn Leu Ser Leu Pro Val Pro Gly Ala Pro Pro 320                                      330
ACCCCAGCCCAGCCCTACTCCTTGCTGCCAGGGGCCCAGCCCTGCTGTGCTGCTCTCCCA
Thr Pro Ala Gln Pro Tyr Ser Leu Leu Pro Gly Ala Gln Pro Cys Cys Ala Ala Leu Pro 340                                      350
GGGACCATGAGGCCCCTACATGTCCGCACCACCTCGGATGGAGGTTACTCTTTCAAGTAT
Gly Thr Met Arg Pro Leu His Val Arg Thr Thr Ser Asp Gly Gly Tyr Ser Phe Lys Tyr

360
GAGACAGTGCCCAACCTTCTCACGCAGCACTGTGCTTGTATCTAAGGGTGGGGGGTCTTC
Glu Thr Val Pro Asn Leu Leu Thr Gln His Cys Ala Cys Ile
```

TABLE I-continued

```
CTTCTTAATCCCATGGCTGGTGGCCACGCCCCCACCATCATCAGCTGGGAGGAAAGGCAG
AGTTGGGAAATAGATGGC
```

Such peptides are often administered in the form of pharmaceutically acceptable nontoxic salts, such as acid addition salts, or in the form of metal complexes, e.g., with zinc, iron or the like (which are considered to be equivalents for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used. Intravenous administration in isotonic saline, phosphate buffer solutions or the like may be effected. Long-lasting preparations may be prepared by combining the active component with poly(lactide-co-glycolide).

Inhibin should be administered under the guidance of a physician, and pharmaceutical compositions will usually contain an effective amount of the peptide in conjunction with a conventional, pharmaceutically-acceptable carrier. The dosage will vary depending upon the specific purpose for which the protein is being administered, and dosage levels in the range of about 0.1 to about 1 milligrams per Kg. of body weight per day may be used when the protein is administered on a regular basis as a male contraceptive.

Although the method of purification of inhibin has been described primarily in terms of isolation from pFF, inhibin can be similarly purified from other crude extracts.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed:

1. A synthetic protein produced using recombinant DNA techniques or the like having two chains interconnected by disulfide bonding, said first chain having formula: H-Ser-Thr-Pro-Leu-Met-Ser-Trp-Pro-Trp-Ser-Pro-Ser-Ala-Leu-Arg-Leu-Leu-Gln-Arg-Pro-Pro-Glu-Glu-Pro-Ala-Ala-His-Ala-Asn-Cys-His-Arg-Val-Ala-Leu-Asn-Ile-Ser-Phe-Gln-Glu-Leu-Gly-Trp-Glu-Arg-Trp-Ile-Val-Tyr-Pro-Pro-Ser-Phe-$R_{65}$-Phe-His-Tyr-Cys-His-Gly-Gly-Cys-Gly-Leu-His-Ile-Pro-Pro-Asn-Leu-Ser-Leu-Pro-Val-Pro-Gly-Ala-Pro-Pro-Thr-Pro-Ala-Gln-Pro-Tyr-Ser-Leu-Leu-Pro-Gly-Ala-Gln-Pro-Cys-Cys-Ala-Ala-Leu-Pro-Gly-Thr-Met-Arg-Pro-Leu-His-Val-Arg-Thr-Thr-Ser-Asp-Gly-Gly-Tyr-Ser-Phe-Ly -Tyr-Glu-Thr-Val-Pro-Asn-Leu-Leu-Thr-Gln-His-Cys-Ala-Cys-Ile-OH, wherein $R_{65}$ is Ile or Arg, and said second chain having either the formula: H-Gly-Leu-Glu-Cys-Asp-Gly-Lys-Val-Asn-Ile-Cys-Cys-Lys-Lys-Gln-Phe-Phe-Val-Ser-Phe-Lys-Asp-Ile-Gly-Trp-Asn-Asp-Trp-Ile-Ile-Ala-Pro-Ser-Gly-Tyr-His-Ala-Asn-Tyr-Cys-Glu-Gly-Glu-Cys-Pro-Ser-His-Ile-Ala-Gly-Thr-Ser-Gly-Ser-Ser-Leu-Ser-Phe-His-Ser-Thr-Val-Ile-A n-His-Tyr-Arg-Met-Arg-Gly-His-Ser-Pro-Phe-Ala-Asn-Leu-Lys-Ser-Cys-Cys-Val-Pro-Thr-Lys-Leu-Arg-Pro-Met-Ser-Met-Leu-Tyr-Tyr-Asp-Asp-Gly-Gln-Asn-Ile-Ile-Lys-Lys-Asp-Ile-Gln-Asn-Met-Ile-Val-Glu-Glu-Cys-Gly-Cys-Ser-OH, or the formula: H-Gly-Leu-Glu-Cys-Asp-Gly-Arg-Thr-Asn-Leu-Cys-Cys-Arg-Gln-Gln-Phe-Phe-Ile-Asp-Phe-Arg-Leu-Ile-Gly-Trp-Ser-Asp-Trp-Ile-Ile-Ala-Pro-Thr-Gly-Tyr-Tyr-Gly-Asn-Tyr-Cys-Glu-Gly-Ser-Cys-Pro-Ala-Tyr-Leu-Ala-Gly-Val-Pro-Gly-Ser-Ala-Ser-Ser-Phe-His-Thr-Ala-Val-Val-A n-Gln-Tyr-Arg-Met-Arg-Gly-Leu-Asn-Pro-Gly-Thr-Val-Asn-Ser-Cys-Cys-Ile-Pro-Thr-Lys-Leu-Ser-Thr-Met-Ser-Met-Leu-Tyr-Phe-Asp-Asp-Glu-Tyr-Asn-Ile-Val-Lys-Arg-Asp-Val-Pro-Asn-Met-Ile-Val-Glu-Glu-Cys-Gly-Cys-Ala-OH.

2. A synthetic peptide according to claim 1 wherein $R_{65}$ is Ile.

3. A synthetic peptide according to claim 1 wherein $R_{65}$ is Arg.

4. A synthetic inhibin protein having the sequence: Ser-Thr-Pro-Leu-Met-Ser-Trp-Pro-Trp-Ser-Pro-Ser-Ala-Leu-Arg-Leu-Leu-Gln-Arg-Pro-Pro-Glu-Glu-Pro-Ala-Ala-His-Ala-Asn-Cys-His-Arg-Val-Ala-Leu-Asn-Ile-Ser-Phe-Gln-Glu-Leu-Gly-Trp-Glu-Arg-Trp-Ile-Val-Tyr-Pro-Pro-Ser-Phe-$R_{65}$-Phe-His-Tyr-Cys-His-Gly-Gly-Cys-Gly-Leu-His-Ile-Pro-Pro-Asn-Leu-Ser-Leu-Pro-Val-Pro-Gly-Ala-Pro-Pro-Thr-Pro-Ala-Gln-Pro-Tyr-Ser-Leu-Leu-Pro-Gly-Ala-Gln-Pro-Cys-Cys-Ala-Ala-Leu-Pro-Gly-Thr-Met-Arg-Pro-Leu-His-Val-Arg-Thr-Thr-Ser-Asp-Gly-Gly-Tyr-Ser-Phe-Ly -Tyr-Glu-Thr-Val-Pro-Asn-Leu-Leu-Thr-Gln-His-Cys-Ala-Cys-Ile or the sequence: Met-Val-Leu-His-Leu-Leu-Leu-Phe-Leu-Leu-Leu-Thr-Pro-Gln-Gly-Gly-His-Ser-Cys-Gln-Gly-Leu-Glu-Leu-Ala-Arg-Glu-Leu-Val-Leu-Ala-Lys-Val-Arg-Ala-Leu-Phe-Leu-Asp-Ala-Leu-Gly-Pro-Pro-Ala-Val-Thr-Arg-Glu-Gly-Gly-Asp-Pro-Gly-Val-Arg-Arg-Leu-Pro-Arg-Arg-His-Ala-Leu Gly-Gly-Phe-Thr-His-Arg-Gly-Ser-Glu-Pro-Glu-Glu-Glu-Glu-Asp-Val-Ser-Gln-Ala-Ile-Leu-Phe-Pro-Ala-Thr-Asp-Ala-Ser-Cys-Glu-Asp-Lys-Ser-Ala-Ala-Arg-Gly-Leu-Ala-Gln-Glu-Ala-Glu-Glu-Gly-Leu-Phe-Arg-Tyr-Met-Phe-Arg-Pro-Ser-Gln-His-Thr-Arg-Ser-Arg-Gln-Val-Thr-Ser Ala-Gln-Leu-Trp-Phe-His-Thr-Gly-Leu-Asp-Arg-Gln-Gly-Thr-Ala-Ala-Ser-Asn-Ser-Ser-Glu-Pro-Leu-Leu-Gly-Leu-Leu-Ala-Leu-Ser-Pro-Gly-Gly-Pro-Val-Ala-Val-Pro-Met-Ser-Leu-Gly-His-Ala-Pro-Pro-His-Trp-Ala-Val-Leu-His-Leu-Ala-Thr-Ser-Ala-Leu-Ser-Leu-Leu-Thr-His-Pro Val-Leu-Val-Leu-Leu-Leu-Arg-Cys-Pro-Leu-Cys-Thr-Cys-Ser-Ala-Arg-Pro-Glu-Ala-Thr-Pro-Phe-Leu-Val-Ala-His-Thr-Arg-Thr-Arg-Pro-Pro-Ser-Gly-Gly-Glu-Arg-Ala-Arg-Arg-Ser-Thr-Pro-Leu-Met-Ser-Trp-Pro-Trp-Ser-Pro-Ser-Ala-Leu-Arg-Leu-Leu-Gln-Arg-Pro-Pro-Glu-Glu-Pro Ala-Ala-His-Ala-Asn-Cys-His-Arg-Val-Ala-Leu-Asn-Ile-Ser-Phe-Gln-Glu-Leu-Gly-Trp-Glu-Arg-Trp-Ile-Val-Tyr-Pro-Pro-Ser-Phe-$R_{65}$-Phe-His-Tyr-Cys-His-Gly-Gly-Cys-Gly-Leu-His-Ile-Pro-Pro-Asn-Leu-Ser-Leu-Pro-Val-Pro-Gly-Ala-Pro-Pro-Thr-Pro-Ala-Gln-Pro-Tyr-Ser-Leu-Leu-Pro-Gly-Ala-Gln-Pro-Cys-Cys-Ala-Ala-Leu-Pro-Gly-Thr-Met-Arg-Pro-Leu-His-Val-Arg-Thr-Thr-Ser-Asp-Gly-Gly-Tyr-Ser-Phe-Ly -Tyr-Glu-Thr-Val-Pro-Asn-Leu-Leu-Thr-Gln-His-Cys-Ala-Cys-Ile, wherein $R_{65}$ is Ile or Arg.

5. A protein according to claim 4 wherein $R_{65}$ is Ile.

6. A synthetic inhibin protein segment of a protein in accordance with claim 4, which segment is effective to create antibodies which neutralize the FSH-release-inhibiting property of human inhibin.

7. A synthetic segment in accordance with claim 6 wherein said segment constitutes the N-terminal 6-residue sequence Ser-Thr-Pro-Leu-Met-Ser or the 25-residue sequence Ser-Thr-Pro-Leu-Met-Ser-Try-Pro-Trp-Ser-Pro-Ser-Ala-Leu-Arg-Leu-Leu-Gln-Arg-Pro-Pro-Glu-Glu-Pro-Ala of the α-chain of of human inhibin.

* * * * *

UNITED STATES PATENT AND TRADEMARK OFFICE
CERTIFICATE OF CORRECTION

PATENT NO. :   4,737,578
DATED      :   April 12, 1988
INVENTOR(S):   Ronald M. Evans et al.

It is certified that error appears in the above-identified patent and that said Letters Patent is hereby corrected as shown below:

Face of Patent, Abstract, line 16, Change "P e" to --Phe--.
Column 1, line 14, Insert --.-- (period) after "activity".
Column 1, line 40, Insert --.-- (period) after "technology".
Column 1, line 48, Before "basal" 1st occurrence insert --inhibiting--.
Column 2, line 11, Change "(??-HPLC)" to --(RP-HPLC)--.
Column 3, line 50, Change "Ly" to --Lys--.
Column 3, line 63, Change "A n" to --Asn--.
Column 4, line 6,  Change "A n" to --Asn--.
Column 7, line 59, Change "Ly" to --Lys--.
Column 7, line 67, Change "A n" to --Asn--.
Column 8, line 15, Change "A n" to --Asn--.
Column 8, lines 34 and 65, Change "Ly" to --Lys--.
Column 8, line 47, Change "Ser Ala" to --Ser-Ala--.
Column 8, line 52, Change "Pro Val" to --Pro-Val--.

Signed and Sealed this

Fourth Day of October, 1988

Attest:

DONALD J. QUIGG

*Attesting Officer*       *Commissioner of Patents and Trademarks*